US009199071B2

(12) United States Patent
Carbunaru (10) Patent No.: US 9,199,071 B2
(45) Date of Patent: Dec. 1, 2015

(54) SYSTEMS AND METHODS FOR MAKING AND USING IMPLANTABLE ELECTRICAL SYSTEMS WITH LEADS THAT COUPLE TO MULTIPLE CONNECTOR PORTS

(71) Applicant: BOSTON SCIENTIFIC NEUROMODULATION CORPORATION, Valencia, CA (US)

(72) Inventor: Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 481 days.

(21) Appl. No.: 13/767,677

(22) Filed: Feb. 14, 2013

(65) Prior Publication Data

US 2013/0218154 A1    Aug. 22, 2013

Related U.S. Application Data

(60) Provisional application No. 61/599,743, filed on Feb. 16, 2012.

(51) Int. Cl.
| | |
|---|---|
| *A61N 1/05* | (2006.01) |
| *A61N 1/372* | (2006.01) |
| *A61B 18/18* | (2006.01) |
| *A61N 1/375* | (2006.01) |
| *H01R 24/58* | (2011.01) |
| *H01R 25/00* | (2006.01) |

(52) U.S. Cl.
CPC . *A61N 1/05* (2013.01); *A61B 18/18* (2013.01); *A61N 1/372* (2013.01); *A61N 1/3752* (2013.01); *H01R 24/58* (2013.01); *H01R 25/006* (2013.01); *H01R 2201/12* (2013.01)

(58) Field of Classification Search
CPC ... A61N 1/3752; A61N 1/3754; A61N 1/375; A61N 1/05; A61N 1/372; A61B 18/18; H01R 2201/12; H01R 24/58; H01R 25/006
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,672,734 B2 | 3/2010 | Anderson et al. |
| 7,761,165 B1 | 7/2010 | He et al. |

(Continued)

*Primary Examiner* — Amanda Patton
(74) *Attorney, Agent, or Firm* — Lowe Graham Jones PLLC; Bruce E. Black (57) ABSTRACT

An electrical stimulation system includes a lead and a connector assembly. The lead includes electrodes, a first terminal array, a second terminal array, and conductors electrically coupling the electrodes to the terminal arrays. The connector assembly includes a first connector port that is open at opposing ends and that electrically couples to the first terminal array. The connector assembly also includes a second connector port that is open at a first end and electrically couples to the second terminal array. The lead and connector assembly simultaneously receive a first portion of the lead, containing the first terminal array, within the first connector port; extend a second portion of the lead out of one end of the first connector port and into the second connector port; and receive a third portion of the lead, containing the second terminal array, within the second connector port of the connector assembly.

20 Claims, 8 Drawing Sheets

(56) References Cited

U.S. PATENT DOCUMENTS

| | | |
|---|---|---|
| 7,949,395 B2 | 5/2011 | Kuzma |
| 7,974,706 B2 | 7/2011 | Moffitt et al. |
| 8,175,710 B2 | 5/2012 | He |
| 2005/0165465 A1 | 7/2005 | Pianca et al. |
| 2007/0150036 A1 | 6/2007 | Anderson |

SYSTEMS AND METHODS FOR MAKING AND USING IMPLANTABLE ELECTRICAL SYSTEMS WITH LEADS THAT COUPLE TO MULTIPLE CONNECTOR PORTS

CROSS-REFERENCE TO RELATED APPLICATIONS

This application claims the benefit under 35 U.S.C. §119 (e) of U.S. Provisional Patent Application Ser. No. 61/599,743 filed on Feb. 16, 2012, which is incorporated herein by reference.

FIELD OF THE INVENTION

The present invention is directed to the area of implantable electrical systems and methods of making and using the systems. The present invention is also directed to implantable electrical systems having leads that couple to multiple connector ports, as well as methods for making and using the systems, leads, and connector ports.

BACKGROUND

Implantable electrical stimulation systems have proven therapeutic in a variety of diseases and disorders. For example, spinal cord stimulation systems may be implanted in the spinal cord to treat chronic pain syndromes and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue including subcutaneous nerves such as the occipital nerve.

In general, a stimulator includes a control module (with a pulse generator), one or more leads, a paddle body connected to the distal end of the lead(s), and an array of stimulator electrodes mounted on the paddle body. The stimulator electrodes are placed in contact with (or near) the nerves, muscles, or other tissue to be stimulated. The pulse generator in the control module generates electrical pulses that are delivered through the electrodes to body tissue.

BRIEF SUMMARY

In one embodiment, an electrical stimulation system includes a lead having a distal end, a proximal end, and a longitudinal length. The lead includes a plurality of electrodes disposed along the distal end of the lead; a first terminal array disposed along the proximal end of the lead; a second terminal array disposed along the proximal end of the lead and proximal to, and spaced-apart from, the first terminal array; and a plurality of conductors electrically coupling the electrodes to the first terminal array and to the second terminal array. A connector assembly is configured and arranged for receiving the lead. The connector assembly includes a first connector port having a first end and an opposing second end and forms a continuous passageway therebetween. The first connector port is open at each of the first and second ends. A first array of connector contacts is disposed in the first connector port and is configured and arranged to electrically couple to the first terminal array. The connector assembly also includes a second connector port having a first end and an opposing second end and forms a continuous passageway therebetween. The second connector port is open at the first end. A second array of connector contacts is disposed in the second connector port and is configured and arranged to electrically couple to the second terminal array. The lead and connector assembly are configured and arranged for simultaneously receiving a first portion of the lead, containing the first terminal array, within the first connector port of the connector assembly; extending a second portion of the lead out of the second end of the first connector port and into the first end of the second connector port; and receiving a third portion of the lead, containing the second terminal array, within the second connector port of the connector assembly. The second portion of the lead is between the first portion of the lead and the third portion of the lead.

In another embodiment, an implantable electrical system includes a lead having a distal end, a proximal end, and a longitudinal length. The lead includes a plurality of electrodes disposed along the distal end of the lead. A first terminal array is disposed along the proximal end of the lead and includes a plurality of terminals. Adjacent terminals of the first terminal array are separated from one another along the longitudinal length of the lead by an intra-array center-to-center spacing. A second terminal array is disposed along the proximal end of the lead such that the second terminal array is proximal to the first terminal array. The second terminal array includes a plurality of terminals. Adjacent terminals of the second terminal array are separated from one another along the longitudinal length of the lead by the intra-array center-to-center spacing. A plurality of conductors electrically couple the electrodes to the first terminal array and to the second terminal array. A first implantable medical device is configured and arranged to electrically couple to the lead. A first connector is disposed on the first implantable medical device and is configured and arranged to receive a portion of the lead containing the first terminal array. The first connector includes a first connector port having a first end and an opposing second end and forms a continuous passageway therebetween. The first connector port is open at each of the first and second end. A first array of connector contacts is disposed in the first connector port and is configured and arranged to electrically couple to the first terminal array. A second implantable medical device is configured and arranged to electrically couple to the lead. A second connector is disposed on the second implantable medical device and is configured and arranged to receive a portion of the lead containing the second terminal array. The second connector includes a second connector port having a first end and an opposing second end and forms a continuous passageway therebetween. The second connector port is open at the first end. A second array of connector contacts is disposed in the second connector port and is configured and arranged to electrically couple to the second terminal array.

In yet another embodiment, an electrical stimulation system includes a lead having a distal end, a proximal end, and a longitudinal length. The lead includes a plurality of electrodes disposed along the distal end of the lead. A first terminal array is disposed along the proximal end of the lead. A second terminal array is disposed at the proximal end of the lead such that the second terminal array is proximal to the first terminal array. The second terminal array is spaced-apart from the first terminal array along the longitudinal length of the lead. A plurality of conductors electrically couple the electrodes to the first terminal array and to the second terminal array. A connector assembly is configured and arranged for receiving the lead. The connector assembly includes a first connector port having a first end and an opposing second end and forms a continuous passageway therebetween. The first connector port is open at each of the first and second ends. A first array of connector contacts is disposed in the first connector port and is configured and arranged to electrically couple to the first terminal array. A second port has a first end and an opposing second end and forms a continuous passageway therebetween. The second connector port is open at the first end. A second array of connector contacts is disposed in the second connector port and is configured and arranged to electrically couple to the second terminal array. A lead insertion tool is configured and arranged to facilitate insertion of the lead into at least one of the first connector port or the second connector port by pulling the proximal end of the lead through at least one of the first connector port or the second connector port.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DETAILED DESCRIPTION

Embodiments of the present disclosure relate to electrical stimulation systems and related methods of use. Suitable implantable electrical stimulation systems include, but are not limited to, an electrode lead ("lead") with a plurality of electrodes disposed on a distal end of the lead and a plurality of terminals disposed on one or more proximal ends of the lead. The leads include one or more conductors that extend along a length of the lead and electrically couple at least one of the electrodes to at least one of the terminals. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; and U.S. Patent Application Publications Nos. 2005/0165465 and 2007/0150036, all of which are incorporated by reference.

In the following sections, embodiments of the present disclosure will be described with reference to spinal cord stimulation. It will be understood that this choice is merely exemplary and that the electrical stimulation system may be utilized in any other region of the body, such as the brain, urinary system, or any other organ or tissue that can be stimulated.

Electrical stimulation systems may include connectors for coupling together two more components. The connectors may be disposed on a first component and used to couple the first component to a second component. For example, a control module may include a connector for coupling a lead to the control module. The connectors may provide a mechanical connection, an electrical connection, or both. In at least some embodiments, the connectors define ports for receiving portions of the second components. When an electrical connection is desired, a given connector may include one or more connector contacts that are disposed in the port and that are configured and arranged to make an electrical connection with the second component. For example, when a proximal end of the lead is inserted into the connector port, connector contacts within the port may form electrical connections with terminals of the inserted lead.

In some cases, an electrical stimulation system may include one or more lead extensions, adaptors, splitters, or combinations thereof to broaden the functionality of the electrical stimulation system. For example, an electrical stimulation system may include a lead extension with opposing first and second ends to increase the distance between the electrodes of the lead and the control module. The lead extensions, adaptors, splitters, or the like, may each include one or more connectors. For example, in the case of an electrical stimulation system with a lead extension, the lead extension may include a first connector (with, optionally, connector contacts disposed therein) to receive the lead, and a control module may include a second connector to receive the lead extension (which, optionally, may include lead extension terminals disposed thereon).

In some cases, the number of connector contacts in a connector contact array of a connector may not be equal to the number of terminals (e.g., terminals of a lead, terminals of a lead extension, or the like) in an elongated member (e.g., a lead, a lead extension, or the like). For example, in some cases a lead with an array of 16 terminals may be used with a connector with two connectors, where each of the connectors includes 8 connector contacts. In which case, the lead might be coupled to an adaptor, or splitter, or the like to divide the 16 terminals into two sets of 8 terminals, which may then enable the terminals to be inserted into the two control module connectors each having 8 connector contacts. Such a configuration, however, may be fragile, or bulky, or both. Additionally, connecting such a configuration may increase procedural time and expense. Such a configuration also introduces additional electrical components into the system, thereby potentially increasing the possibility of developing a faulty electrical connection in the system.

As herein described, an implantable electrical system includes a lead that includes a plurality of spaced-apart terminal arrays, and a connector with a plurality of connector ports, where each of the different connector ports is configured and arranged to receive a different one of the terminal arrays. In at least some embodiments, a lead insertion tool may be used to facilitate insertion of the lead into one or more of the connector ports. The connector ports may be disposed on control modules, lead extensions, adaptors, splitters, or the like or combinations thereof. It will be understood that connector can be disposed on other implantable medical devices in addition to, or in lieu of the above-mentioned devices including, for example, an EEG system, an RF heating system, an RF ablation system, or the like of combinations thereof.

The implantable electrical system includes a lead having either a single proximal end or a plurality of proximal ends. The plurality of connector ports can be disposed on a single device, or the plurality of connector ports can be disposed on a plurality of different devices. The implantable electrical system may include any suitable number of connector ports including, for example, one, two, three, four, five, six, seven, eight, or more connector ports. The implantable electrical system may include any suitable number of medical devices on which the connector ports are disposed including, for example, one, two, three, four, five, six, seven, eight, or more medical devices.

Figure 1:
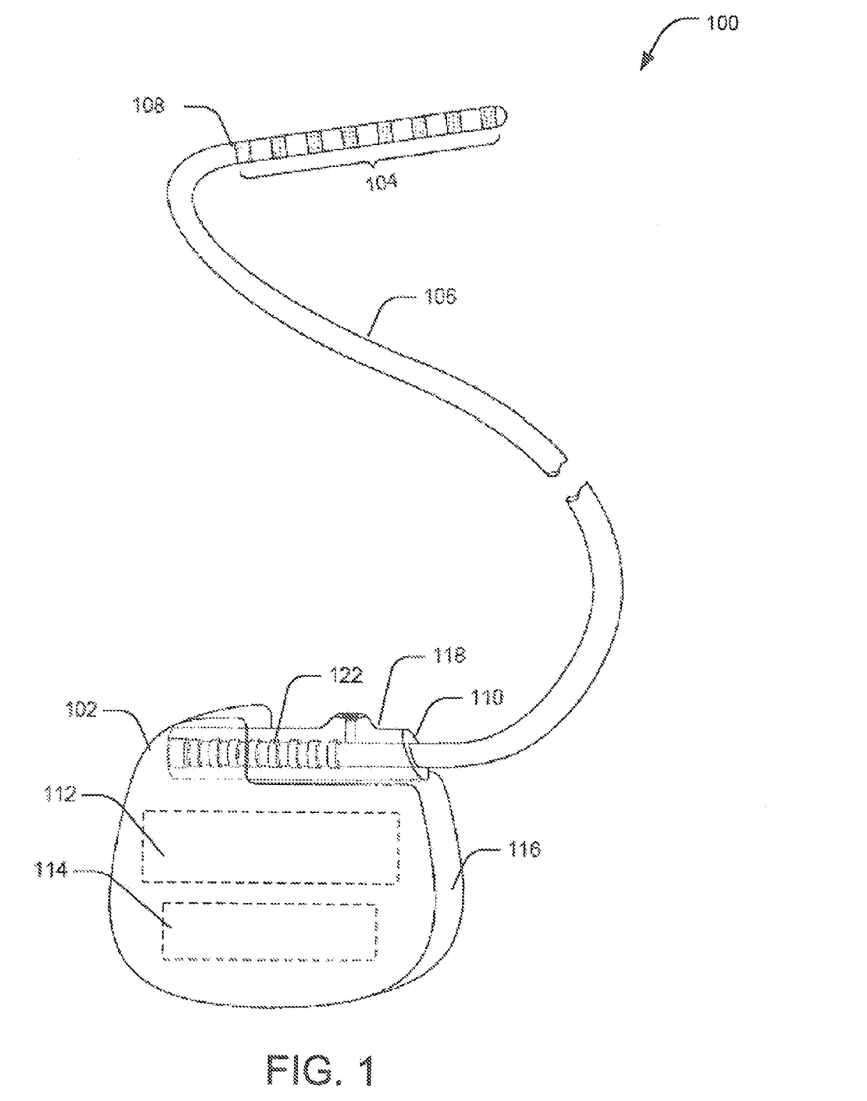
FIG. 1 is a schematic perspective view of a stimulation system, the stimulation system including a control module and a lead inserted into the control module, according to the invention.

FIG. 1 illustrates an exemplary electrical stimulation system 100 adapted to perform a desired medical procedure. The electrical stimulation system 100 includes a control module 102, a plurality of electrodes 104, and at least one lead 106 coupling the plurality of electrodes to the control module. The control module may include a stimulator or pulse generator for providing electrical pulses to the electrodes 104 for stimulating patient tissue. In at least some embodiments, the electrodes 104 are disposed on a distal end 108 of the lead 106, while the control module 102 is connected to a proximal end 110 of the lead 106.

One or more components of the electrical stimulation system 100 are typically implanted into a patient's body for a variety of applications including, but not limited to, brain stimulation, neural stimulation, spinal cord stimulation, or muscle stimulation. For example, a portion of the lead 106 containing the electrodes 104 may be implanted in the patient's body, at or adjacent a target region, and the control module 102 may be situated outside the patient's body, for example strapped to the patient's arm, wrist, or taped around her chest. Alternatively, the entire stimulation system 100 may be implanted in the patient's body. The electrodes 104 may be implanted at the target area, and the control module 102 may be implanted in any suitable area within the body large enough to accommodate it, such as the abdominal cavity.

The control module 102 typically includes an electronic subassembly 112 (including the pulse generator and a processor) and an optional power source 114 disposed in a sealed housing 116. The control module 102 also includes a connector 118 into which the proximal end 110 of the lead 106 can be plugged to make an electrical connection via conductive contacts 122 on the control module 102 and terminals (202 of FIG. 2) disposed on the proximal end 110 of the lead 106.

The control module 102 generates electrical impulses, which are provided to the electrodes 104 via the terminals (202 of FIG. 2) and the conductors of the lead 106. These electrical impulses disrupt pain signals transmitted to the brain from the target nerve, muscle, or organ, thereby reducing or eliminating pain sensed by the patient. Depending on the degree of pain and the target location, in some embodiments physicians or operators may, optionally, regulate or modify the strength, duration, and period between impulses using a remote controller (not shown). The remote controller may be external to the patient's body, and may communicate with the control module 102 through known techniques.

The electrodes 104 may be configured in any arrangement at the distal end of the lead. One configuration commonly used in percutaneous stimulation, as depicted in FIG. 1, includes multiple electrodes positioned along the distal portion of the elongated lead 106. In another configuration, the electrodes 104 may be placed on a paddle (not shown), which has a multiplicity of electrode contacts spread out over a flat, paddle-like surface that forms the distal end 108 of the lead 106. A paddle lead permits the electrode contacts to be spaced apart to provide wider coverage over a stimulation area.

The electrodes 104 can be formed using any conductive, biocompatible material. Examples of suitable material include metals, alloys, conductive polymers, and conductive carbon. The number of electrodes disposed on the lead 106 may vary depending on the target area, and the condition being treated. For example, there may be two, four, six, eight, ten, twelve, fourteen, sixteen, or more electrodes. As will be recognized, other number of electrodes may also be used.

The electrodes 104 conduct electrical current pulses to stimulate nerve fibers, muscle fibers, or other body tissues. In at least some embodiments, a processor, within the control module 102, is included to control the activation, timing and electrical characteristics of the stimulation system. For example, the processor can, if desired, control one or more of the timing, frequency, strength, duration, and waveform of the pulses generated by the pulse generator. In addition, the processor can selectively activate the electrodes for stimulation.

Figure 2:
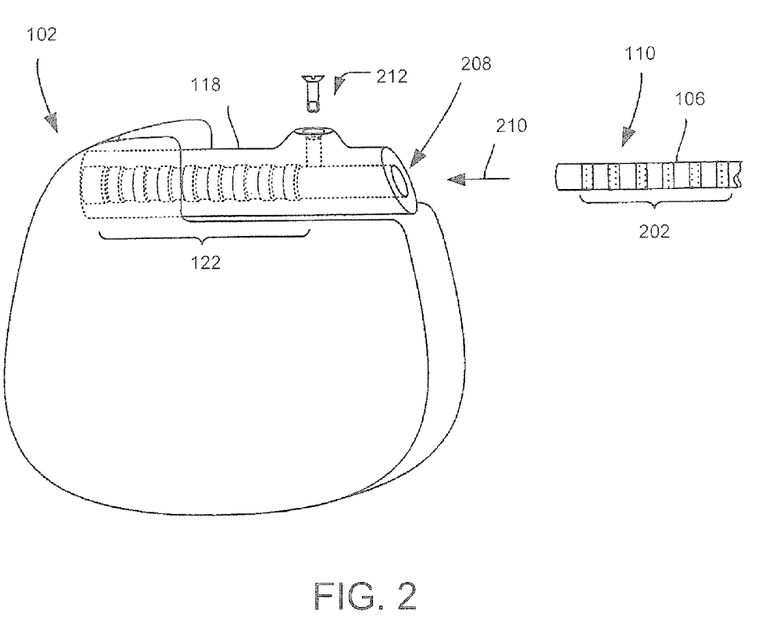
FIG. 2 is a schematic perspective view of one embodiment of a proximal portion of the lead of FIG. 1 insertable into the control module of FIG. 1, according to the invention.

FIG. 2 illustrates one embodiment of the proximal end 110 of the lead 106 and the control module 102 of the stimulation system 100. As shown in FIG. 2, terminals 202 are disposed at the proximal end 110 of the lead 106 for connection to corresponding connector contacts 122 disposed on the connector 118 of the control module 102. Conductive wires ("conductors") (not shown) extend along the lead from the terminals 202 to the electrodes 104. Typically, one or more electrodes 104 are electrically coupled to a given terminal 202. In some embodiments, each of the terminals 202 is only connected to one electrode 104. The conductors may be embedded in the non-conductive material of the lead 106, or the conductors may be disposed in one or more lumens (not shown) extending along the lead 106. In some embodiments, there is an individual lumen for each conductor. In other embodiments, two or more conductors may extend through a single lumen.

In FIG. 2, the lead 106 is adapted and arranged for insertion into the control module 102. The connector 118 defines a port 208 into which the proximal end 110 of lead 106 with terminals 202 can be inserted, as shown by directional arrow 210. The port 208 includes multiple connector contacts 122. When the lead 106 is inserted into the port 208, the connector contacts 122 can be aligned with the terminals 202 to electrically couple the control module 102 to the electrodes (104 in FIG. 1). In at least some embodiments, the terminals 202 and the connector contacts 122 are designed so that each terminal 202 aligns with a corresponding connector contact 122 on the connector 118.

Optionally, the lead 106 and the connector 118 may include corresponding retaining features to fasten the lead 106 to the connector 118, once adequate placement of the lead 106 within the port 208 is achieved. The lead 106 may include a reinforced surface region (312 in FIG. 3A) to which one or more fasteners (e.g., one or more set screws, pins, or the like) 212 may fasten against via a fastener aperture, such as a threaded aperture. Any suitable number of corresponding retaining features can be implemented. In at least some embodiments, a single set of corresponding retaining features are used. In at least some embodiments where multiple connectors 118 are used, the number of sets of corresponding retaining features is equal to the number of connector ports.

The lead 106 typically contains multiple electrodes and multiple corresponding terminals. In order to provide electrical current to each of the electrodes 104, each of the terminals 202 is aligned with a corresponding connector contact 122 in the connector port 208. For example, the connector port 208 may include eight connector contacts 122 that each align with a different terminal 202 of the lead 106. As described above, when the number of terminals 202 exceeds the number of connector contacts 122, it may be necessary to add additional devices to the lead 106 or to the control module 102 to provide electrical current to each terminal 202. For example, splitters or adaptors may be used to electrically couple multiple terminals 202 to the connector contacts 122.

Figure 3A:
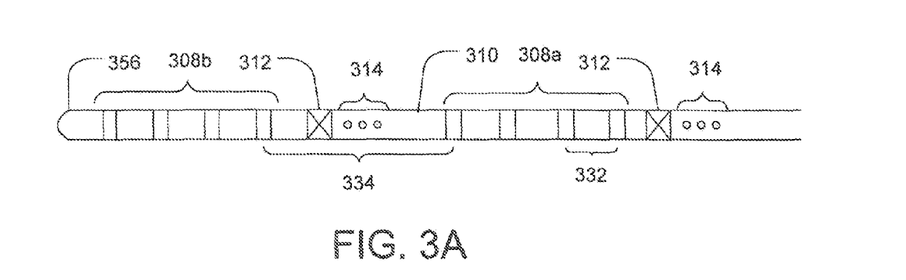
FIG. 3A is a schematic side view of one embodiment of two arrays of terminals disposed on a proximal portion of a lead, according to the invention.
Figure 3B:
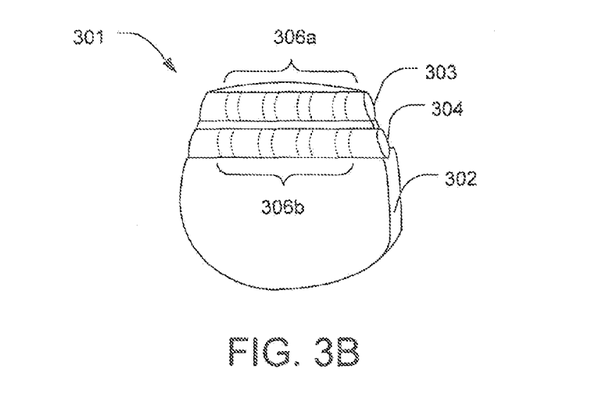
FIG. 3B is a schematic perspective view of another embodiment of a control module, the control module defining a plurality of connector ports, each connector port configured and arranged to receive a different one of the terminal arrays of FIG. 3A, according to the invention.
Figure 4:
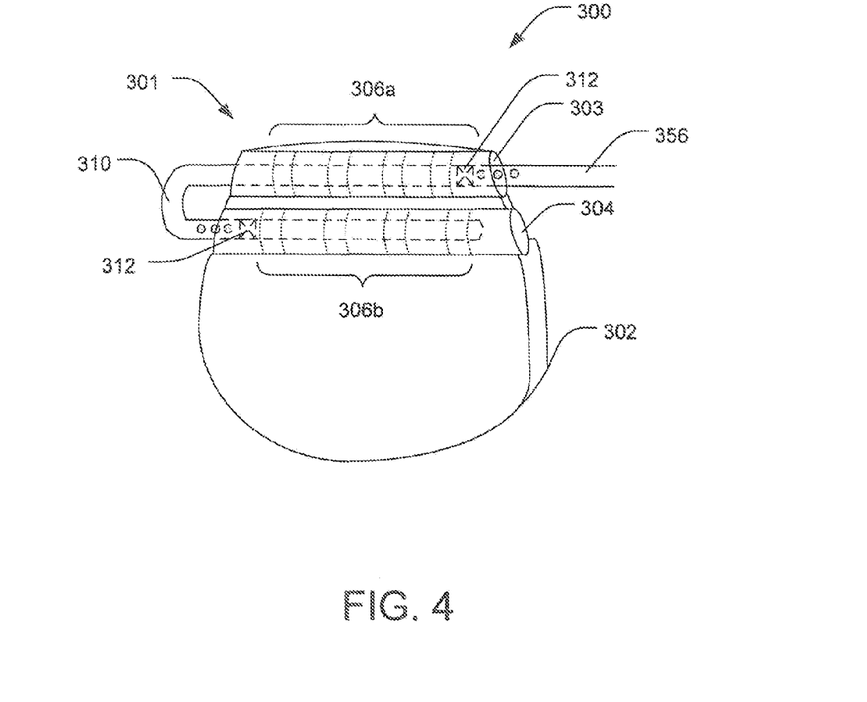
FIG. 4 is a schematic perspective view of one embodiment of the lead of FIG. 3A inserted into the control module of FIG. 3B, according to the invention.

FIG. 3A depicts one embodiment of the proximal end of a lead 356. FIG. 3B depicts one embodiment of a control module 302 with a connector assembly 301 having plurality of connector ports for receiving the lead 356. FIG. 4 depicts one embodiment of the lead 356 electrically coupled to the control module 302.

As shown in FIG. 3A, the lead 356 includes terminals arranged into two arrays, including a first terminal array 308a and a second terminal array 308b that is spaced apart longitudinally (i.e., axially) along the lead 106 from the first terminal array 308a. For each of the terminal arrays 308a, 308b the terminal array includes a plurality of terminals, where adjacent terminals of the terminal array are separated from one another along the longitudinal length of the lead by an intra-array center-to-center spacing, such as intra-array center-to-center spacing 332.

A terminal-array spacer region 310 may be disposed between the first terminal array 308a and the second terminal array 308b. The terminal-array spacer region 310 provides an inter-array spacing between the first terminal array 308a and the second terminal array 308b.

The terminal-array spacer region 310 can be formed from any suitable material and can have a flexibility that is greater than, less than, or equal to the remaining portions of the lead 356. In at least some embodiments, the terminal-array spacer region 310 is of sufficient length to enable bending of the lead 356. In at least some embodiments, the terminal-array spacer region 310 is of sufficient length and flexibility to enable bending of the lead 356 90°, 120°, 150°, 180°, or more along a longitudinal length of the terminal-array spacer region 310.

In at least some embodiments, the terminal-array spacer region 310 has a length such that a terminal of the first terminal array 308a disposed closest to the second terminal array (e.g., the proximal-most terminal of the first terminal array 308a), and a terminal of the second terminal array 308b disposed closest to the first terminal array (e.g., the distal-most terminal of the second terminal array 308b) are separated from one another along the longitudinal length of the lead by an inter-array center-to-center spacing 334. In at least some embodiments, the inter-array center-to-center spacing 334 is at least two, three, four, or five times larger than the intra-array center-to-center spacing 332. In at least some embodiments, the inter-array center-to-center spacing 334 is no greater than ten, nine, eight, seven, six, five, four, or three times the intra-array center-to-center spacing 332. In at least some embodiments, the inter-array center-to-center spacing 334 is no less than two times the spacing of the intra-array center-to-center spacing 332 and no greater than seven times the spacing of the intra-array center-to-center spacing 332.

In FIG. 3B and FIG. 4, the control module 302 includes a connector assembly 301 having a first port 303 and a second port 304. In at least some embodiments, the first port 303 and the second port 304 are disposed in a side-by-side arrangement, where the ports extend parallel to one another along any axis (e.g., top/bottom, left/right, up/down, or the like) in any relative orientation (e.g., across from one another, one of the ports disposed over top of the other of the ports, or the like). In at least some embodiments, the first port 303 extends from a first end to an opposing second end such that the first port 303 is open at both opposing ends and forms a continuous passageway therethrough. In at least some embodiments, the second port 304 extends from a first end to an opposing second end such that the second port 304 is open at both opposing ends and forms a continuous passageway therethrough. In other embodiments, the second port 304 extends from one end and is closed at the opposing end such that the second port 304 is open from one end and closed at the opposing end. In at least some embodiments, the open end of the second port 304 is in proximity to the second end of the first port 303 such that the open end of the second port 304 is closer to the second end of the first port 303 than to the first end of the first port 303.

As shown in FIG. 4, a first connector contact array 306a is disposed in the first port 303, and a second connector contact array 306b is disposed in the second port 304. The connector contacts 306a, 306b and the terminal arrays 308a, 308b are similar in structure and operation to the connector contacts 122 and the terminals 202, respectively, of FIG. 2.

In FIG. 3B and FIG. 4, each port 303, 304 in the control module 302 includes four connector contacts in each of the connector contact arrays 306a, 306b. It will be understood that the number of connector contacts in a given port may vary, as desired. The number of connector ports can be less than, greater than, or equal to the number of terminal arrays disposed on the lead. The number of connector contacts within each connector contact array can be no less than, no greater than, or equal to the number of terminals in each terminal array.

Optionally, the lead 356 may include one or more retention features 312 to removably fasten the lead within the connectors via the one or more fasteners (212 in FIG. 2). The retention feature 312 may be implemented in any suitable manner, as described above with reference to fastener 212 of FIG. 2. In at least some embodiments, the retention feature 312 is implemented as a reinforced surface region covering a portion of the surface of the lead to which the fastener (see, for example fastener 212 in FIG. 2) may be tightened against to retain an inserted lead in a given port without piercing the lead 106. FIG. 4 shows two retention features 312, with one of the two retention features in communication with the port 303, and the other of the two retention features in communication with the port 304. It will be understood that the number of retention features may vary, as desired.

Optionally, the lead 356 may include one or more alignment markers 314 to assist a medical practitioner in insuring proper axial alignment between the terminals 308a, 308b and their corresponding connector contacts 306a, 306b. The one or more alignment markers 314 generally represent reference point(s) for aligning the terminals with corresponding connector contacts, as will be explained later in relation with FIGS. 3C, 3D, and 3E. The alignment markers 314 may be any suitable type of marker known in the art including, for example, radio-opaque markers, texturally-distinct regions (e.g., scored regions, raised regions, depressed regions, or the like), visually-distinct regions (e.g., colored regions, regions of contrasting colors, patterns, shapes, number, letters, symbols, or other indicia), or the like or combinations thereof. In at least some embodiments, the alignment markers 314 may be visible through a transparent or translucent portion of the connector.

Figure 3C:
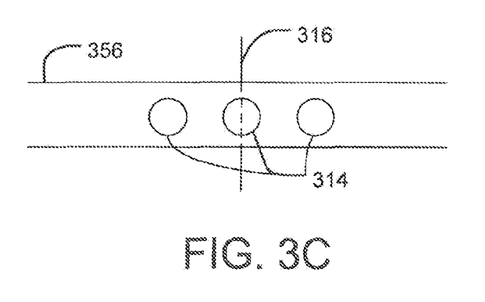
FIGS. 3C, 3D, and 3E are schematic close-up views of one embodiment of alignment markers of the lead of FIG. 3A inserted different amounts into a connector port, according to the invention.
Figure 3D:
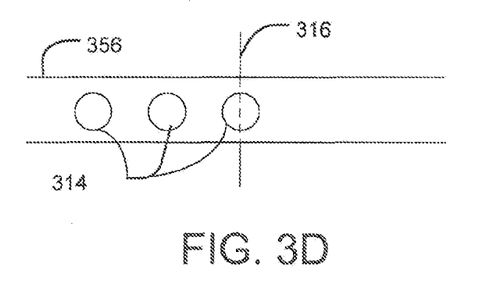
Figure 3E:
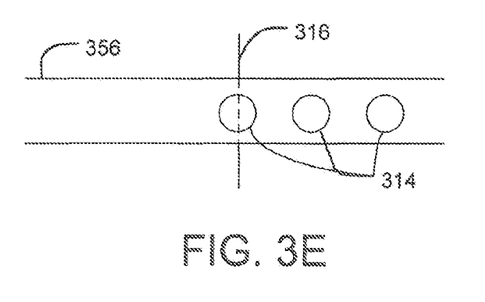

FIGS. 3C, 3D, and 3E illustrate one embodiment of three alignment markers 314. In FIGS. 3C-3E, the lead 106 is shown being inserted into the first port 303 from a first end of the port (right hand side of FIGS. 3C, 3D, and 3E) towards an opposing second end of the first port 303 (left hand side of FIGS. 3C, 3D, and 3E). Dashed line 316 in FIGS. 3C, 3D, and 3E represents an outer wall of the first end of the first port 303. The three alignment markers 314 are arranged so that, when the lead 106 is properly aligned within the first port 303 (i.e., when the lead 356 is inserted an appropriate distance within the first port 303), the middle alignment marker of the three alignment markers 314 is aligned with the dashed line 316. FIG. 3D shows a scenario where the lead 356 has been inserted too deep into the first port 303, and the first-side alignment marker of the three alignment markers 314 is aligned with the dashed line 316. FIG. 3E shows a scenario where the lead 56 has not been inserted deep enough into the first port 303, and the second-side alignment marker of the three alignment markers 314 is aligned with the dashed line 316.

FIG. 4 illustrates one embodiment of an electrical stimulation system 300. As shown in FIG. 4, the lead 356 is inserted into the connector assembly 301 such that the first end of the lead 356 is inserted into the first port 303, and extends outwardly from the second end of the first port 303. The terminals of the second terminal array 308b align with the connector contacts of the second connector contact array 306b. The lead 356 is bent approximately 180° along the terminal-array spacer region 310 and is inserted into the second port 304. The terminals of the first terminal array 308a align with the connector contacts of the first connector contact array 308a.

It will be understood that, in alternate embodiments, the lead 56 may be inserted concurrently into more than two connector ports. For example, the lead 356 may be inserted into a connector assembly defining three ports, four ports, or more ports, in a manner similar to that described above, and shown in FIG. 4. In at least some embodiments, each of the ports is open at both ends. In other embodiments, each of the ports but one are open at both ends, where the last port is open at one end and closed at the opposing end.

Figure 5A:
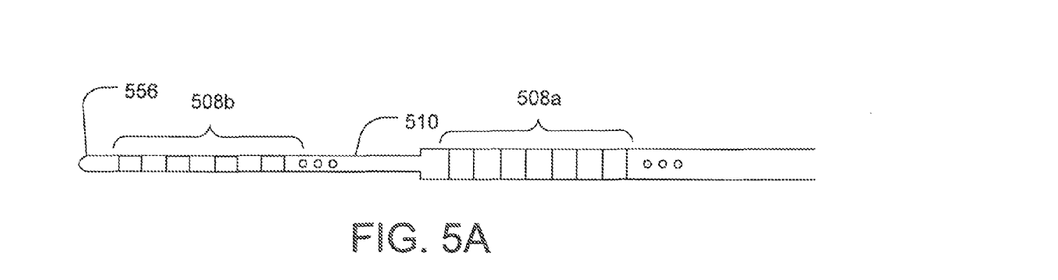
FIG. 5A is a schematic side view of another embodiment of a proximal end of a lead, the lead having a first terminal array with a first diameter and a second terminal array with a second diameter that is different from the diameter of the first terminal array, according to the invention.
Figure 5B:
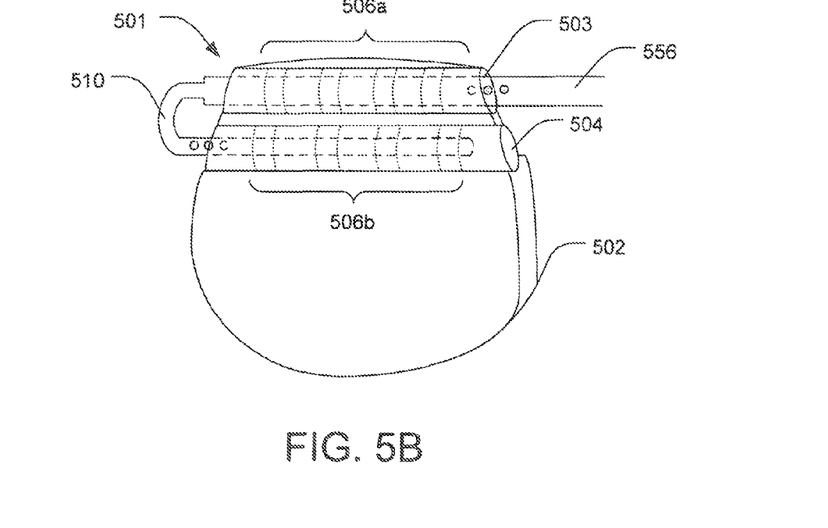
FIG. 5B is a schematic perspective view of one embodiment of the proximal portion of the lead of FIG. 5A inserted into a plurality of connector ports defined in a control module, according to the invention.

FIGS. 5A and 5B depict another embodiment of an electrical stimulation system 500 that includes a lead 556 and a control module 502. FIG. 5A shows a first terminal array 508a and a second terminal array 508b longitudinally-spaced-apart from one another at the proximal end of the lead 556 such that the second terminal array 508b is more proximal along the lead 556 than the first terminal array 508a. The first terminal array 508a is separated from the second terminal array 506b by a terminal-array spacer region 510. The second terminal array 508b is disposed on a proximal-most portion of the lead 556, which has a diameter that is smaller than adjacent portions of the lead 556. In at least some embodiments, the lead is isodiametric except for the smaller-diameter proximal-most portion of the lead 556.

In at least some embodiments, the second terminal array 506b has a diameter that is smaller than a diameter of the first terminal array 506a. In at least some embodiments, the second terminal array 506b has a diameter that is no more than 90%, 80%, 70%, 60%, 50% as large as a diameter of the first terminal array 506a.

The terminal-array spacer region 510 may be of any suitable diameter. In some embodiments, the terminal-array spacer region 510 is the same diameter as the first terminal array 506a. In other embodiments, the terminal-array spacer region 510 is the same diameter as the second terminal array 506a. In yet other embodiments, the terminal-array spacer region 510 has a diameter that is no greater than the first terminal array 506a and no less than the second terminal array 506b.

In FIG. 5B, the control module 502 includes a connector assembly 501 defining a first port 503 and a second port 504. In at least some embodiments, the lead 556 enters a first end of the first port 503, and extends outwardly from a second end of the first port 503, opposite to the first end. The terminals of the second terminal array 308b align with the connector contacts of the second connector contact array 306b. The lead 556 bends approximately 180° along the terminal-array spacer region 510 and enters the second port 504. The terminals of the first terminal array 508a align with the connector contacts of the first connector contact array 508a.

The difference in diameter between the proximal-most region of the lead and the remaining portions of the lead may serve as a stop to modulate insertion of the lead 556 into the ports 503, 504 and electrical alignment between terminals and corresponding connector contacts. For example, the port 504 may be sized (e.g., have a diameter) that enables the second terminal array 506b to be inserted into the port 504, but which is sized to prevent the first terminal array 506a, or the portion of the lead on which the first terminal array 506a is disposed, from being inserted into the port 504. In at least some embodiments, the second port 503 has a diameter that is no more than 90%, 80%, 70%, 60%, 50% as large as a diameter of the first port 503.

The difference in diameters of the terminal arrays 506a, 506b and the ports 503, 504 may also serve to provide instruction as to how to properly insert the lead 556 into the ports 503, 504. For example, the different sizes of the terminal arrays 506a, 506b and the ports 503, 504 may provide a visual cue that the terminal array 506a corresponds with the port 503, and the terminal array 506b corresponds with the port 504.

Conventional leads may have proximal ends that are laterally stiff enough to facilitate insertion of the lead into a connector. In at least some cases, the proximal end of the conventional leads are laterally stiffer at the proximal end of the lead than in a middle section between the terminals and the electrodes. In at least some embodiments, the electrical stimulation system includes an insertion tool for facilitating insertion of the lead 356, 556 into the connector ports. In which case, the proximal end of the lead may be formed to be more floppy than proximal ends of at least some conventional leads. In at least some embodiments, the proximal end of the lead 356, 556 is no more laterally stiff at the proximal end of the lead than in a middle section of the lead (e.g., between the terminals and the electrodes).

Figure 6:
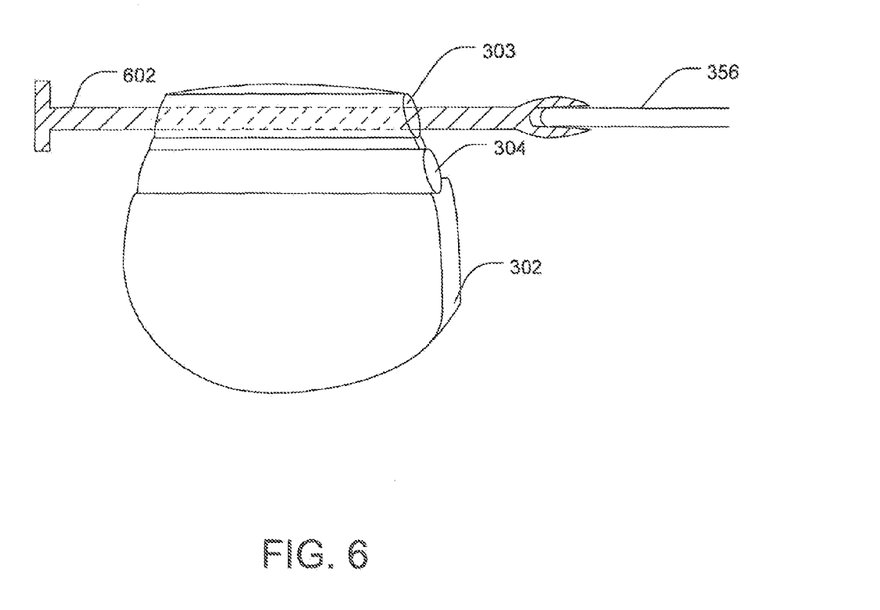
FIG. 6 is a schematic perspective view of one embodiment of a lead insertion tool disposed in a connector port of the control module of FIG. 3B, the lead insertion tool coupled to a proximal end of the lead of FIG. 3A, according to the invention.

FIG. 6 illustrates one embodiment of the lead 356 being inserted into the first connector port 303 using an insertion tool 602. In at least some embodiments, the insertion tool 602 pulls the lead 106 through the first port 303, instead of pushing the lead 356 using a lead-receiving feature (e.g., a knob, hook, loop, tab, opposable gripping members, or the like) disposed on one end of the insertion tool 602. The insertion tool 602 can be used to facilitate insertion of the lead into either, or both, of the ports 302 and 304. In at least some embodiments, the insertion tool 602 may be inserted through the second end of the first port 303 to grab and releasably retain the lead 356. In at least some embodiments, the insertion tool 602 may be pre-loaded into the control module 302. In at least some embodiments, the insertion tool 602 may serve as a port plug when the lead 356 is not disposed along the entire length of the first port 303.

In at least some embodiments, a tool-receiving feature (e.g., a knob, hook, loop, tab, divot, or the like) is disposed on the proximal tip of the lead 356 which enables the insertion tool 602 to firmly hold and retain the lead 356, such that pulling of the insertion tool 602 causes a corresponding movement of the lead 356 without damaging the lead. Using the insertion tool 602 may enable a more flexible proximal end of the lead 356 from conventional proximal ends of leads, as the lateral strength of the proximal end of the lead 356 is not critical for the insertion of the lead 356 into the first port 303. It may be advantageous to enable proximal ends of lead to be floppy. Such an arrangement may simplify manufacturing. Additionally, such an insertion tool 602 may obviate the need to replace leads 356 due to minor proximal end damage that may compromise the lateral stiffness of the proximal end of the lead.

It will be understood that, in embodiments of lead with multiple proximal ends, each proximal end, or one or more (but less then all) of the proximal ends may include longitudinally-spaced-apart terminal arrays. It will further be understood that the connector port configurations described herein may also be used in conjunction with lead extensions. It will also be understood that, in at least some embodiments, connector ports may be bidirectional, enabling lead insertion through either the first or the opposing second end of a given port.

The connector ports can be disposed on a single device (e.g., a control module, a lead extension, or the like), or on a plurality of different devices. In at least some embodiments, the devices are medical devices. In at least some embodiments, the devices are implantable devices.

Figure 7:
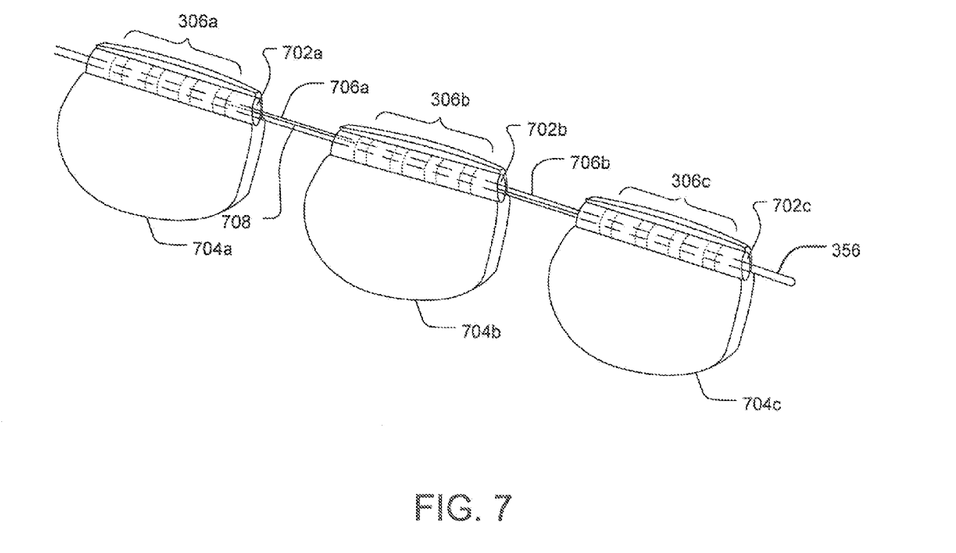
FIG. 7 is a schematic perspective view of one embodiment of a plurality of terminal arrays disposed on a proximal portion of the lead of FIG. 3A, each of the terminal arrays being received by a different connector port of a different implantable medical device, according to the invention.

FIG. 7 illustrates one embodiment of a plurality of terminal arrays 306a-c disposed on the lead 356. Each of the terminal arrays 306a-c is received by a different connector port 702a-c of a different device 704a-c (e.g., an implantable medical device), respectively. Thus, each of the multiple devices 704a-c is coupled to a single lead 106. The devices 704a-c may have similar or different functions. For example, in at least some embodiments at least one of the devices 704a-c may be a control module, while at least one of the 704a-c may be an RF ablating system, or an EEG recording system, or both.

Terminal-array spacer region 706a is disposed between the terminal arrays 306a and 306b, and terminal-array spacer region 706b is disposed between the terminal arrays 306b and 306c. At least one of the terminal-array spacer regions 306a,b may be flexible, to aid in the placement within a patient of the various implantable devices. In at least some embodiments, at least one of the terminal-array spacer regions 306a,b may be rigid, as illustrated in FIG. 7. The amount of rigidity may, in some cases, be determined by the type and thickness of material chosen for the region 306a,b of the lead 356. It will be understood that the terminal-array spacer region 706a,b may have similar mechanical properties (e.g., length, materials, flexibility, diameter, and the like) as the terminal-array spacer region 310, described above with reference to FIGS. 3A-5B.

Within the lead 356 are conductors that electrically couple the electrodes to the terminals. The implantable devices 704a-c can have common electrical nodes, or may be independent, if the devices are intended to acts independently. In at least some embodiments, some of the terminals may be electrically connected to one or more of the devices 704a-c, while others may not.

In at least some embodiments, at least one conductor 708 extends between one or more terminals of a first terminal array and one or more terminals of a second terminal array without extending to any of the electrodes. For example, in FIG. 7, the conductor 708 extends between the terminal array 306a and the terminal array 306b. This may enable additional features, such as different devices that can communicate with one another, synchronize, or use a common reference. In at least some embodiments, the conductor 708 may facilitate the grounding of two implantable devices 704a-c at the same reference potential, or enable transmission of power between two or more of the implantable devices 704a-c, or synchronize communication activities between the implantable devices 704a-c, or program and control one implantable device 702 though another, or combinations thereof. Additionally, when two implantable devices 702 are microstimulators, this configuration may enable full current steering functionality using the microstimulators.

Embodiments of the present disclosure may be used in any medical or non-medical procedure, including any medical procedure where one or more body part requires electrical stimulation. In addition, at least certain aspects of the aforementioned embodiments may be combined with other aspects of the embodiments, or removed, without departing from the scope of the preset disclosure.

While the present disclosure has been described by means of specific embodiments and applications thereof, numerous modifications and variations could be made thereto by those skilled in the art without departing from the scope of the present disclosure set forth in the claims.

What is claimed as new and desired to be protected by US Letters Patent:

1. An electrical stimulation system comprising:
   a lead having a distal end, a proximal end, and a longitudinal length, the lead comprising
      a plurality of electrodes disposed along the distal end of the lead,
      a first terminal array disposed along the proximal end of the lead,
      a second terminal array disposed along the proximal end of the lead and proximal to, and spaced-apart from, the first terminal array, and
      a plurality of conductors electrically coupling the electrodes to the first terminal array and the second terminal array; and
   a connector assembly configured and arranged for receiving the lead, the connector assembly comprising
      a first connector port having a first end and an opposing second end and forming a continuous passageway therebetween, wherein the first connector port is open at each of the first and second ends, a first array of connector contacts disposed in the first connector port and configured and arranged to electrically couple to the first terminal array, a second connector port having a first end and an opposing second end and forming a continuous passageway therebetween, wherein the second connector port is open at the first end, and a second array of connector contacts disposed in the second connector port and configured and arranged to electrically couple to the second terminal array, wherein the lead and connector assembly are configured and arranged for simultaneously receiving a first portion of the lead, containing the first terminal array, within the first connector port of the connector assembly; extending a second portion of the lead out of the second end of the first connector port and into the first end of the second connector port; and receiving a third portion of the lead, containing the second terminal array, within the second connector port of the connector assembly, wherein the second portion of the lead is between the first portion of the lead and the third portion of the lead.

2. The system of claim 1, wherein the second connector port is open at the second end.

3. The system of claim 1, wherein the second connector port is closed at the second end.

4. The system of claim 1, wherein the first connector port and the second connector port are arranged on the connector assembly in a side-by-side configuration.

5. The system of claim 1, further comprising a control module, the control module configured and arranged to electrically couple to the lead, the control module comprising
a housing, and
an electronic subassembly disposed in the housing, the electronic subassembly comprising a pulse generator configured and arranged for providing stimulation pulses to the plurality of electrodes.

6. The system of claim 5, wherein the connector assembly is disposed on the control module.

7. The system of claim 5, further comprising a lead extension having a distal end and a proximal end, wherein the connector assembly is disposed on the distal end of the lead extension and the proximal end of the lead extension is configured and arranged to electrically couple with the control module.

8. The system of claim 1, wherein the first terminal array has a first diameter and the second terminal array has a second diameter that is equal to the first diameter.

9. The system of claim 1, wherein the first terminal array has a first diameter and the second terminal array has a second diameter that is different from the first diameter.

10. The system of claim 9, wherein the second diameter is no more than 90% as large as the first diameter.

11. The system of claim 1, wherein the first connector port has a first port diameter and the second connector port has a second port diameter that is different from the first port diameter.

12. The system of claim 11, wherein the second port diameter is no more than 90% as large as the first port diameter.

13. The system of claim 1, wherein the lead further comprises at least one conductor that extends between the first terminal array and the second terminal array without extending to any of the plurality of electrodes.

14. A method for implanting an electrical stimulation system, the method comprising:
advancing the electrical stimulation system of claim 1 into a body of a patient;
extending the proximal end of the lead into the first end of the first connector port and out the second end of the first connector port;
aligning the first terminal array of the lead with the first array of connector contacts;
inserting a portion of the lead extending from the second end of the first connector port into the second connector port; and
aligning the second terminal array of the lead with the second array of connector contacts.

15. An implantable electrical system comprising:
a lead having a distal end, a proximal end, and a longitudinal length, the lead comprising
a plurality of electrodes disposed along the distal end of the lead,
a first terminal array disposed along the proximal end of the lead, the first terminal array comprising a plurality of terminals, wherein adjacent terminals of the first terminal array are separated from one another along the longitudinal length of the lead by an intra-array center-to-center spacing,
a second terminal array disposed along the proximal end of the lead and proximal to the first terminal array, the second terminal array comprising a plurality of terminals, wherein adjacent terminals of the second terminal array are separated from one another along the longitudinal length of the lead by the intra-array center-to-center spacing, and
a plurality of conductors electrically coupling the electrodes to the first terminal array and the second terminal array;
a first implantable medical device configured and arranged to electrically couple to the lead;
a first connector disposed on the first implantable medical device and configured and arranged to receive a portion of the lead containing the first terminal array, the first connector comprising
a first connector port having a first end and an opposing second end and forming a continuous passageway therebetween, wherein the first connector port is open at each of the first and second end,
a first array of connector contacts disposed in the first connector port and configured and arranged to electrically couple to the first terminal array,
a second implantable medical device configured and arranged to electrically couple to the lead;
a second connector disposed on the second implantable medical device and configured and arranged to receive a portion of the lead containing the second terminal array, the second connector comprising
a second connector port having a first end and an opposing second end and forming a continuous passageway therebetween, wherein the second connector port is open at the first end, and
a second array of connector contacts disposed in the second connector port and configured and arranged to electrically couple to the second terminal array.

16. The system of claim 15, wherein at least one of the first implantable medical device or the second implantable medical device is a control module comprising
a housing, and
an electronic subassembly disposed in the housing, the electronic subassembly comprising a pulse generator for providing stimulation pulses to the plurality of electrodes.

17. The system of claim 15, wherein at least one of the first implantable medical device or the second implantable medical device is an EEG system, an RF heating system, or an RF ablation system.

18. The system of claim 15, wherein a terminal of the first terminal array disposed closest to the second terminal array, and a terminal of the second terminal array disposed closest to the first terminal array are separated from one another along the longitudinal length of the lead by an inter-array center-to-center spacing, and wherein the inter-array center-to-center spacing is at least three times larger than the intra-array center-to-center spacing.

19. An electrical stimulation system comprising:
   a lead having a distal end, a proximal end, and a longitudinal length, the lead comprising
      a plurality of electrodes disposed along the distal end of the lead,
      a first terminal array disposed along the proximal end of the lead,
      a second terminal array disposed at the proximal end of the lead and proximal to the first terminal array, wherein the second terminal array is spaced-apart from the first terminal array along the longitudinal length of the lead, and
      a plurality of conductors electrically coupling the electrodes to the first terminal array and the second terminal array; and
   a connector assembly configured and arranged for receiving the lead, the connector assembly comprising
      a first connector port having a first end and an opposing second end and forming a continuous passageway therebetween, wherein the first connector port is open at each of the first and second ends,
      a first array of connector contacts disposed in the first connector port and configured and arranged to electrically couple to the first terminal array,
      a second port having a first end and an opposing second end and forming a continuous passageway therebetween, wherein the second connector port is open at the first end, and
      a second array of connector contacts disposed in the second connector port and configured and arranged to electrically couple to the second terminal array; and
   a lead insertion tool configured and arranged to facilitate insertion of the lead into at least one of the first connector port or the second connector port by pulling the proximal end of the lead through at least one of the first connector port or the second connector port.

20. The system of claim 19, wherein the lead insertion tool comprises a lead-receiving feature configured and arranged to removably retain the proximal end of the lead while pulling the proximal end of the lead through at least one of the first connector port or the second connector port.

* * * * *